United States Patent
Alreemi et al.

(10) Patent No.: US 12,258,321 B1
(45) Date of Patent: Mar. 25, 2025

(54) ARYL-1,2,3-TRIAZOLE COMPOUNDS, PHARMACEUTICAL COMPOSITION THEREOF AND METHOD FOR TREATMENT OF BREAST CANCER

(71) Applicants: Roaa M. Alreemi, Jeddah (SA); Hind A. Alkhatabi, Jeddah (SA); Mohammed A. Baradwan, Jeddah (SA); Abdelsattar M. Omar, Jeddah (SA); Moustafa E. El-Araby, Cairo (EG); Yara E. Mansour, Cairo (EG); Samar S. Fatahala, Cairo (EG); Ahmed M. Said, Cairo (EG); Shahenda Mahgoub, Cairo (EG)

(72) Inventors: Roaa M. Alreemi, Jeddah (SA); Hind A. Alkhatabi, Jeddah (SA); Mohammed A. Baradwan, Jeddah (SA); Abdelsattar M. Omar, Jeddah (SA); Moustafa E. El-Araby, Cairo (EG); Yara E. Mansour, Cairo (EG); Samar S. Fatahala, Cairo (EG); Ahmed M. Said, Cairo (EG); Shahenda Mahgoub, Cairo (EG)

(73) Assignees: University of Jeddah, Jeddah (SA); King Abdulaziz University, Cairo (EG); Helwan University, Cairo (EG)

( * ) Notice: Subject to any disclaimer, the term of this patent is extended or adjusted under 35 U.S.C. 154(b) by 0 days.

(21) Appl. No.: 18/914,691

(22) Filed: Oct. 14, 2024

(51) Int. Cl.
| | |
|---|---|
| *C07D 249/06* | (2006.01) |
| *A61K 31/4192* | (2006.01) |
| *A61P 31/00* | (2006.01) |
| *A61P 35/00* | (2006.01) |
| *C07D 405/12* | (2006.01) |

(52) U.S. Cl.
CPC ........ *C07D 249/06* (2013.01); *A61K 31/4192* (2013.01); *A61P 31/00* (2018.01); *A61P 35/00* (2018.01); *C07D 405/12* (2013.01)

(58) Field of Classification Search
CPC ..... C07D 249/06; C07D 405/12; A61P 31/00; A61P 35/00; A61K 31/4192
See application file for complete search history.

(56) References Cited

U.S. PATENT DOCUMENTS

2021/0139434 A1* 5/2021 El-Araby ............. C07D 307/52

\* cited by examiner

*Primary Examiner* — Daniel R Carcanague
*Assistant Examiner* — Jerica Katlynn Wilson
(74) *Attorney, Agent, or Firm* — WCF IP

(57) ABSTRACT

Compounds belonging to the group of N-benzyl-2-(4-(4-substituted-1H-1,2,3-triazol-1-yl)phenylacetamides have cytotoxic activities against MCF7 breast cancer cells, and are useful in therapeutic regimes for breast cancer. The N-benzyl-2-(4-(4-substituted-1H-1,2,3-triazol-1-yl)phenylacetamides also have beneficial effects on BAX, BCL-2, MCL-1 and MAPK pathways within MCF& breast cancer cells.

6 Claims, No Drawings

ARYL-1,2,3-TRIAZOLE COMPOUNDS, PHARMACEUTICAL COMPOSITION THEREOF AND METHOD FOR TREATMENT OF BREAST CANCER

FIELD OF THE INVENTION

The invention generally relates to compounds that exhibit enhanced activities against breast cancer cells. In particular, the compounds are 1-phenyl-4-substituted-1H-1,2,3-triazole with activities against breast cancer cell lines.

BACKGROUND

Breast cancer is a complex and heterogeneous disease characterized by the uncontrolled growth of breast tissue cells[1]. It is the most common cancer in women worldwide, and despite significant advances in diagnosis and treatment, it remains a leading cause of cancer-related deaths. According to the World Health Organization (WHO), breast cancer is the most commonly diagnosed cancer in women, with approximately 2.3 million new cases reported globally each year. It accounts for 1 in 4 cancer cases among women and is a significant cause of cancer-related deaths. The incidence of breast cancer varies by region, with higher rates in developed countries, partly due to factors like longer life expectancy, hormonal and reproductive factors, and better screening practices[2].

In the United States, breast cancer affects about 1 in 8 women, making it the second leading cause of cancer death after lung cancer[3]. According to the American Cancer Society (ACS), an estimated 297,790 new cases of invasive breast cancer and 55,720 new cases of DCIS were diagnosed in 2023. Globally, breast cancer has surpassed lung cancer as the most common cancer in women, although survival rates have improved due to early detection and better treatments[4].

Breast cancer is not a single disease but consists of multiple types, each with unique characteristics and treatment responses. The early stage of primary breast tumors is called Ductal Carcinoma In Situ (DCIS) and is considered a non-invasive type of breast cancer. In this stage, abnormal cells are confined to the milk ducts and have not spread to surrounding tissues. DCIS is considered an early form of breast cancer and is highly treatable with a good prognosis if detected early.

If early DCIS type of primary tumor has not been detected cancer spread from the ducts or lobules into surrounding breast tissue. The most common subtypes include Invasive Ductal Carcinoma (IDC) which accounts for about 70-80% of all breast cancers. It begins in the milk ducts but invades nearby tissue, making it more likely to spread to lymph nodes and other parts of the body. Another type of breast cancer, classified as Invasive Lobular Carcinoma (ILC) originates in the milk-producing lobules and constitutes about 10% of breast cancer cases. It tends to grow in a unique pattern, making it harder to detect on imaging. The most life-threatening type is Triple-Negative Breast Cancer (TNBC) that lacks estrogen, progesterone, and HER2 receptors, making it more aggressive and harder to treat with conventional therapies like hormone therapy or HER2-targeted drugs. Other types are HER2-positive and Hormone Receptor-Positive Breast Cancer (HR+) cancers which can be treated effectively if detected early with hormonal or targeted therapies[5].

Several factors contribute to the development of breast cancer, including both non-modifiable and modifiable risks. The risk of developing breast cancer increases with age, with most cases occurring in women over the age of 50 and it is related to genetic factors and family history. Although breast cancer is considered a disease of women, but 1% of cases affect men. Some physiological factors are linked to the incidence of breast cancer such as Early menstruation (before age 12), late menopause (after age 55), and never having children are associated with increased risk. Some risk factors have been implicated to the occurrence of breast cancer such as prolonged use of hormone therapy, alcohol consumption, obesity and low physical activities.

Recently, certain genetic factors have become in the focus as high risk factor such as mutations in certain genes such as BRCA1 and BRCA2 genes. Women with these mutations have up to a 70-80% lifetime risk of developing breast cancer[6-7].

Treatment for breast cancer depends on the stage of the disease, the molecular subtype, and the patient's overall health. Treatment typically involves a combination of surgery, radiation, chemotherapy, hormonal therapy, and targeted therapies.

Chemotherapy of breast cancer may be administered before surgery (neoadjuvant) to shrink tumors or after surgery (adjuvant) to reduce the risk of recurrence. Chemotherapy is particularly important in treating aggressive cancers like TNBC or advanced-stage breast cancer.

The first type of breast cancer chemotherapy is hormonal treatment with tamoxifen and/or aromatase inhibitors which are prescribed to treat hormone receptor-positive breast cancers. The second method of treatment is targeted therapies which were introduced to specifically attack cancer cells while sparing healthy tissues. For instance, HER2-positive breast cancers can be treated with drugs like trastuzumab (Herceptin) and pertuzumab. This approach has revolutionized treatment and improved survival rates. Newer targeted therapies, such as CDK4/6 inhibitors, are used in combination with hormonal therapy for advanced HR+ breast cancers. Despite the effectiveness of current therapies, breast cancer can develop resistance, especially in advanced or metastatic cases. For instance, HR+ cancers may acquire mutations that allow them to grow even in the presence of hormone-blocking drugs. A common mechanism of resistance includes ability of cancer cells may to evade chemotherapy, such as increasing drug efflux or enhancing DNA repair. Recently, some HER2-positive cancers become resistant to drugs like trastuzumab, necessitating the use of second-line treatments such as lapatinib or neratinib. Ongoing research into breast cancer is focused on overcoming drug resistance, improving outcomes for aggressive subtypes, and personalizing treatment approaches.

Drugs like palbociclib, ribociclib, and abemaciclib have been developed to inhibit specific proteins involved in cell division and are used in combination with hormonal therapy for advanced HR+ breast cancer. These inhibitors have been shown to significantly improve progression-free survival in metastatic cases. Another important advance occurred upon the success of immunotherapies to gain approvals for use against aggressive cancers like TNBC. Drugs like pembrolizumab (a PD-1 inhibitor) work by enhancing the immune system's ability to recognize and attack cancer cells. Early results have shown promise, particularly when combined with chemotherapy. PARP inhibitors, such as olaparib and talazoparib, have been also used to treat breast cancers with BRCA mutations. These drugs work by interfering with the cancer cells' ability to repair DNA damage, leading to cell death. The above detailed difficulty, improper response to treatment and development of resistance necessitate continuing research to discovery newer classes of compounds to treat breast cancer[8-9].

SUMMARY OF THE INVENTION

One objective of the invention is to provide therapeutic 1-phenyl-4-substituted-1H-1,2,3-triazole-based compounds and a process of synthesizing these compounds.

A further objective of the invention is to provide a pharmaceutical composition comprising phenyl-4-substituted-1H-1,2,3-triazole-based compounds and a method of treating breast cancer.

Therapies that target antiapoptotic proteins and MAPK signaling constituted an effective strategy to develop a new class of compounds that kill and/or inhibit the growth of breast cancer cells.

The present invention relates to a compound of formula (I)

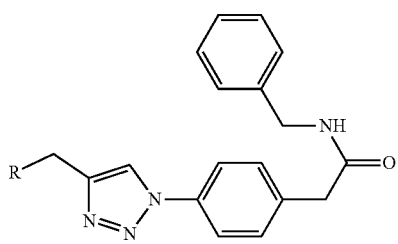

or a salt thereof or a composition thereof,
wherein R is optionally alkyl, alkoxy, alkylamino, alkylthio, phenyl, phenoxy, phenylamino, phenylthiol, hydroxy, amino, aralkyl or heterocyclic group, amidic, ureidic, carboxylic sulfonamido or ester group. Wherein the aforementioned group is optionally substituted with alkyl, aryl, alkoxy, nitrile, nitro, halo or another suitable group.

In one embodiment, compounds are formula II

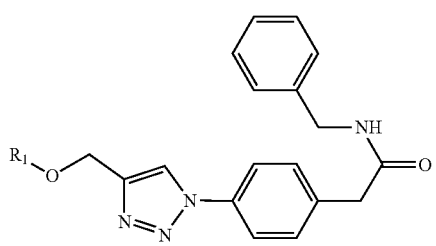

Wherein R1 is optionally selected from H, alkyl, phenyl, substituted phenyl, aralkyl, heterocyclic or heterocyclic methyl. In one embodiment, the compound of Formula (II) is

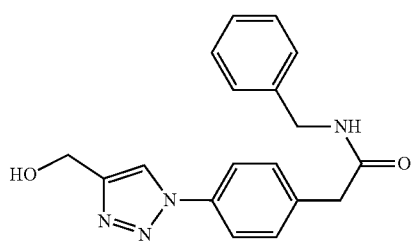 [SMILES: O=C(Cc1ccc(-n2cc(CO)nn2)cc1)NCc1ccccc1]

Exemplary Compounds

Comp 1
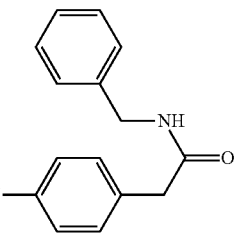

Comp 2
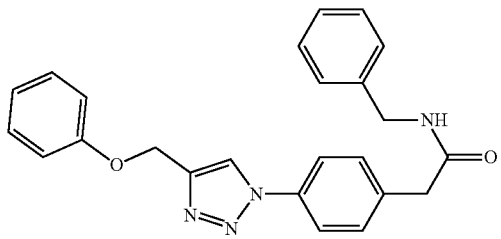

Comp 3
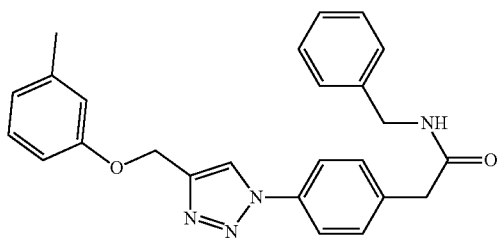

Comp 4
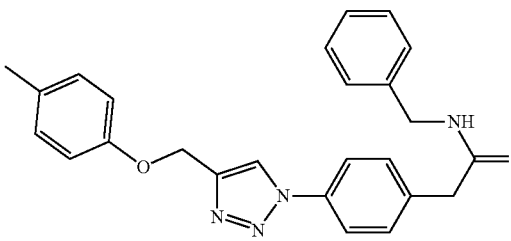

Comp 5
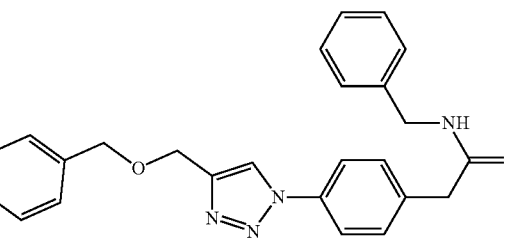

Comp 6
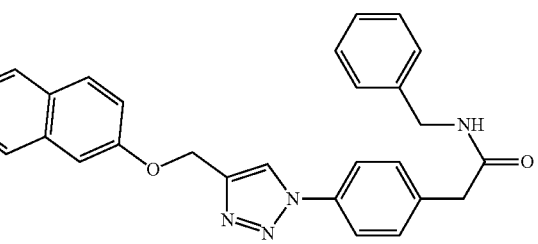

-continued

Comp 7

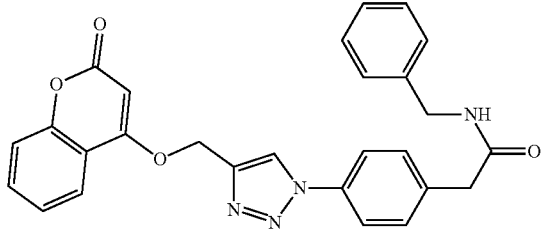

Comp 8

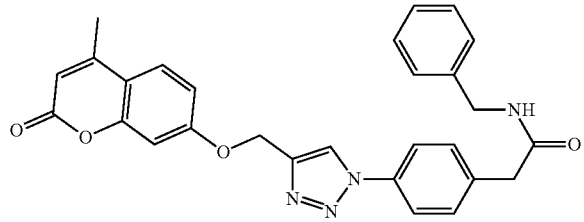

DETAILED DESCRIPTION OF THE EMBODIMENTS

Embodiments of the invention will now be described more fully hereinafter with reference to the accompanying drawings, in which some, but not all, embodiments of the disclosure are shown by example.

As used herein, the term "salt" is intended to an association between a compound of Formula I with a pharmaceutically compatible acid. Examples of such salts include, but are not limited to, salts formed with inorganic acids (for example, hydrochloric acid (HCl), hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalenedisulfonic acid, methanesulfonic acid, p-toluenesulfonic acid and polygalacturonic acid. Other salts include pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

As used herein, the terms "complex", "compound", and "product" are used interchangeably, and are intended to refer to a chemical entity, whether in the solid, liquid or gaseous phase, and whether in a crude mixture or purified and isolated.

In certain embodiments, the compound of formula (II) may be included in addition to, or as a substitute for, the compound of formula (I) within the pharmaceutical composition. As used herein, the term "composition" or "pharmaceutical composition" refers to a mixture containing the active ingredient along with other chemical substances, such as pharmaceutically acceptable carriers and excipients. The purpose of a composition is to facilitate the administration of the compound described in any of its embodiments to a subject. Pharmaceutical compositions of the present disclosure may be prepared using methods well known in the art, such as conventional processes including mixing, dissolving, granulating, levigating, emulsifying, encapsulating, entrapping, or lyophilizing. Depending on the intended method of administration—whether oral, parenteral, or topical—the composition can be formulated as a solid, semi-solid, or liquid dosage form, including tablets, suppositories, pills, capsules, powders, liquids, or suspensions, typically in unit dosage form to allow for precise, single-dose administration.

The term "active ingredient," as used herein, refers to any biologically active component in the composition, such as the compound represented by formula (I), formula (II), or a salt, solvate, tautomer, stereoisomer, or any mixtures thereof. In certain embodiments, additional active ingredients, beyond the compounds described in this disclosure, may also be incorporated into the pharmaceutical composition.

In one or more embodiments, the pharmaceutical composition comprises up to 10% by weight of the pharmaceutically acceptable carrier and/or excipient relative to a total weight of the pharmaceutical composition. In one or more embodiments, the pharmaceutical composition comprises a range from 0.01 wt % up to 99.9 wt % of the compound of formula (I) relative to a total weight of the pharmaceutical composition.

In some embodiments, the composition comprises up to 10 wt % of a pharmaceutically acceptable salt of the compound of formula (I). In some embodiments, the composition comprises up to 10 wt % of a pharmaceutically acceptable solvate of the compound of formula (I). Preferably, the composition may further comprise pharmaceutically acceptable binders, such as sucrose, lactose, xylitol, and pharmaceutically acceptable excipients such as calcium carbonate, calcium phosphate, and dimethyl sulfoxide (DMSO).

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

In one or more embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, but are not limited to, phosphate buffers, citrate buffer, acetate buffers, borate buffers, carbonate buffers, bicarbonate buffers, and buffers with other organic acids and salts.

Exemplary inorganic salts include, but are not limited to, calcium carbonate, calcium phosphate, disodium hydrogen phosphate, potassium hydrogen phosphate, sodium chloride, zinc oxide, zinc sulfate, and magnesium trisilicate.

Exemplary fatty acids include, but are not limited to, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, but are not limited to, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohol, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, any bland fixed oil can be employed including synthetic mono- or di-glycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, PA, 1975; and Liberman, H. A.; Lachman, L., Eds. Pharmaceutical dosage forms, Marcel Decker, New York, NY, 1980, which are incorporated herein by reference in their entirety.

In other embodiments, the pharmaceutical composition having the compound of formula (I), the salt thereof, the solvate thereof, the tautomer thereof, the stereoisomer thereof, or the mixture thereof has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration.

In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the pharmaceutical composition described herein is not a controlled-release composition.

According to another aspect, the present disclosure relates to a method of treating breast cancer. The method involves administering the pharmaceutical composition to a subject in need of therapy.

In one or more embodiments, the pharmaceutical composition administered comprises the compound of formula (I), or a salt thereof or a mixture thereof. In a preferred embodiment, the pharmaceutical composition administered comprises a compound which is:

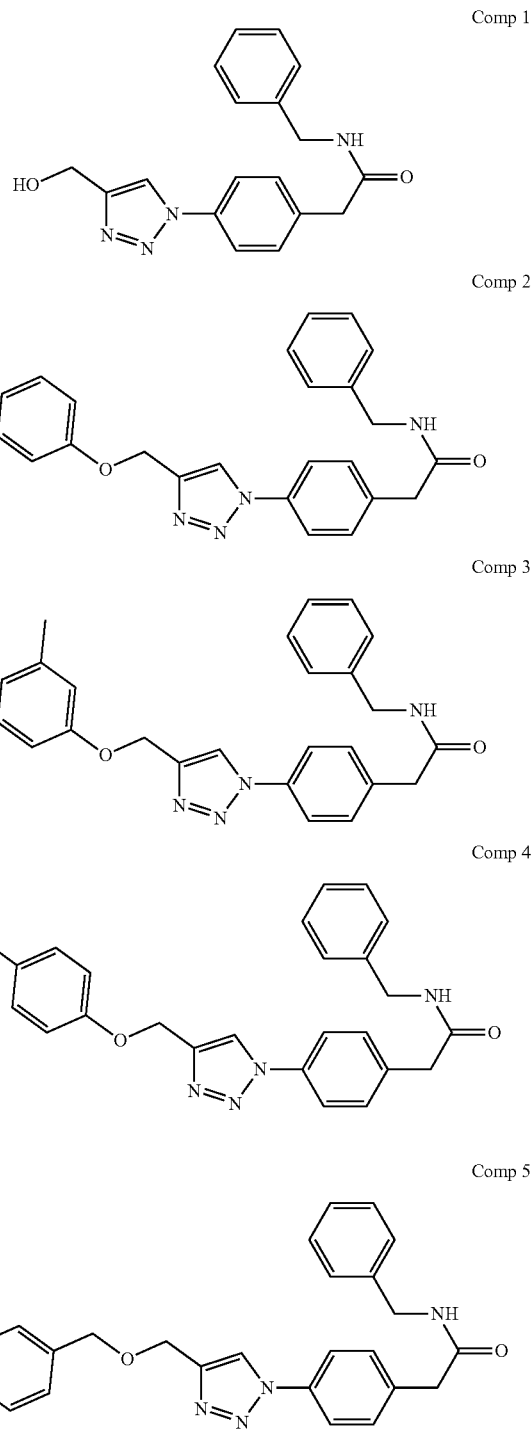

-continued

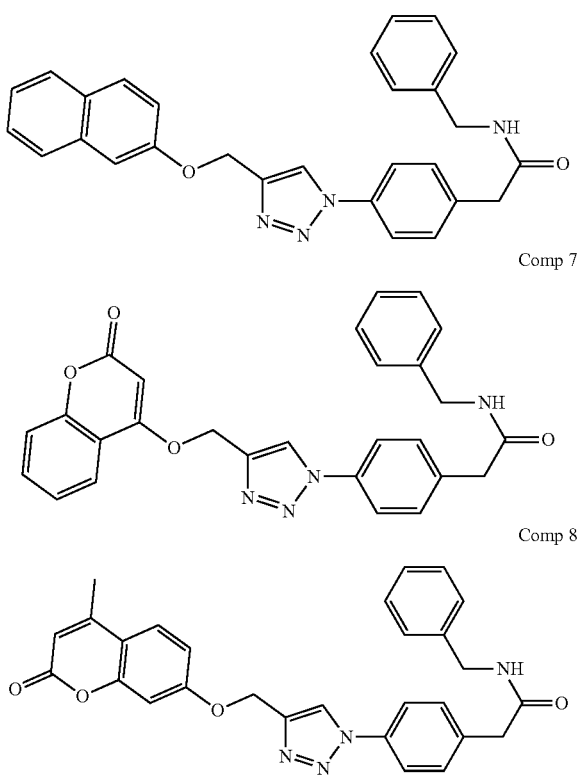

Comp 6

Comp 7

Comp 8

In one embodiment, the compounds of the present disclosure are prepared according to methods known to those of ordinary skills in the art. The following methods set forth below are provided for illustrative purposes and are not intended to limit the scope of the disclosure. The starting amine (1) is reacted with nitrous acid to form a diazonium salt which was instantly reacted with sodium azide to install azide group via SNAr mechanism. The phenyl azide was reacted with variety of alkynes (3) under a click-chemistry cyclization conditions, which required Cu(I) catalyzed conditions to obtain the final 1,2,3-triazole.

The structure of compounds described as Examples in this disclosure are confirmed by several spectral analysis techniques such as proton nuclear magnetic resonance spectroscopy ($^1$H NMR), carbon-13 nuclear magnetic resonance spectroscopy ($^{13}$C NMR), mass spectrometry and ultraviolet-coupled high pressure liquid chromatography (LC-MS).

In one embodiment, the compounds inhibit the growth of breast cancer cell line MCF7 in significant potencies, which in some instances are compared to or exceeding that of a reference drug (Staurosporine). The MCF7 breast cancer cell line is a widely used and well-characterized model for studying breast cancer biology and therapy response. Established from a 69-year-old Caucasian female with metastatic breast cancer, MCF7 cells are luminal A-type, estrogen receptor-positive (ER+), progesterone receptor-positive (PR+), and human epidermal growth factor receptor 2-negative (HER2-)[10]. MCF7 cells are sensitive to tamoxifen, doxorubicin, and trastuzumab, but exhibit resistance to paclitaxel and cisplatin. Resistance to chemotherapy and hormone therapy is a significant clinical concern, with approximately 30-50% of ER+ breast cancers developing resistance to endocrine therapy. MCF7 cells are commonly used to study resistance mechanisms and test novel therapeutic strategies. Clinically, MCF7-like tumors account for approximately 50-60% of breast cancers, with ER+ status being a prevalent feature in approximately 70-80% of cases[11].

In one embodiment, the effect of exemplary disclosed compounds on BAX (BCL-2-Associated X protein) as an apoptotic marker in breast cancer cells was demonstrated. Exposure of MCF7 breast cancer cells to exemplary disclosed compounds resulted in increase in BAX which is a proapoptotic protein that plays a crucial role in regulating cell death and survival. As an apoptotic marker, BAX is involved in the mitochondrial pathway of apoptosis, where it heterodimerizes with anti-apoptotic proteins like BCL-2, neutralizing their protective effects and promoting cell death. Overexpression of BAX has been linked to increased sensitivity to apoptosis, while its downregulation is associated with resistance to apoptosis and tumorigenesis. BAX expression is often evaluated in cancer research to assess the efficacy of therapeutic interventions aimed at inducing apoptosis in cancer cells. Studies have shown that BAX expression is decreased in various types of cancer, including breast, lung, and colon cancer, while its restoration can enhance chemotherapy-induced apoptosis[11-12].

In one embodiment, the effect of exemplary disclosed compounds on BCL-2 (B-cell lymphoma 2) protein as an apoptotic marker in breast cancer cells was demonstrated.

BCL-2 is a key anti-apoptotic protein that regulates cell survival and death. As an apoptotic marker, BCL-2 inhibits mitochondrial outer membrane permeabilization, preventing the release of cytochrome c and subsequent activation of caspases, thereby blocking apoptosis. Overexpression of BCL-2 is associated with cancer development, progression, and resistance to chemotherapy. Elevated BCL-2 levels have been detected in various cancers, including follicular lymphoma, breast, lung, and prostate cancer. Conversely, downregulation of BCL-2 sensitizes cancer cells to apoptosis, enhancing the efficacy of therapeutic interventions. BCL-2 expression is often evaluated in cancer research to assess the likelihood of treatment response and patient prognosis[13-14].

In one embodiment, the effect of exemplary disclosed compounds on MCL-1 as an apoptotic marker in breast cancer cells was demonstrated.

MCL-1 (Myeloid Cell Leukemia-1) is a key anti-apoptotic protein that regulates cell survival and death. As an apoptotic marker, MCL-1 inhibits mitochondrial outer membrane permeabilization, preventing the release of cytochrome c and subsequent activation of caspases, thereby blocking apoptosis. MCL-1 is overexpressed in various cancers, including leukemia, lymphoma, breast, lung, and prostate cancer, contributing to tumorigenesis and chemotherapy resistance. Elevated MCL-1 levels correlate with poor prognosis and reduced patient survival[15]. Conversely, downregulation of MCL-1 sensitizes cancer cells to apoptosis, enhancing the efficacy of therapeutic interventions. MCL-1 expression is often evaluated in cancer research to assess the likelihood of treatment response and patient prognosis[16-17].

In one embodiment, the effect of exemplary compounds on MAPK pathway proteins was demonstrated. The Mitogen-Activated Protein Kinase (MAPK) signaling pathway is a critical regulator of cell growth, differentiation, and survival[18]. In cancer, the MAPK pathway is frequently dysregulated, promoting unchecked cell proliferation and tumor progression. The MAPK pathway consists of a cascade of serine/threonine kinases, including RAF, MEK, and ERK, which are activated by growth factors, cytokines, and other stimuli. Activation of the MAPK pathway leads to phosphorylation and activation of downstream targets, including transcription factors, such as Elk-1 and c-Fos, which regulate gene expression involved in cell growth and survival. In cancer cells, constitutive activation of the MAPK pathway drives cell cycle progression, inhibits apoptosis, and enhances angiogenesis, metastasis, and resistance to chemotherapy. Mutations in MAPK pathway components, such as BRAF and KRAS, are common in various cancers, including melanoma, colorectal, lung, and breast cancer[19-20].

Formulae (I) and (II) exemplified by the novel compounds Comp-1 to Comp-8 may function as new therapeutics either alone or combined with other drugs for treatment of breast cancer based on their cytotoxic activities, apoptotic activities and downregulation of MAPK pathway proteins in MCF7 breast cancer cell line. By treatment we mean reducing or alleviating symptoms of breast cancer or reversing the adverse affects of breast cancer or eliminating breast cancer.

The examples below are intended to further illustrate protocols for preparing, characterizing the compound of formulae (I) and (II), and uses thereof, and are not intended to limit the scope of the claims.

Example 1

Synthesis of screened compounds.

Example 2

Chemical Synthesis: General

Starting materials, solvents and reagents were purchased from Sigma-Aldrich Fine Chemicals (St Louis, MO, USA) and Merck KGaA (Darmstadt, Germany). The progress of reactions was monitored by Thin-layer chromatography (TLC) carried on a silica gel-precoated aluminum sheets (type 60, F 254, Merck KGaA, Darmstadt, Germany). Spots were visualized under the UV light lamp at λmax 254 nm. Hexane: ethyl acetate mixture (3:1) was used as an eluent. Infrared spectra (IR) were recorded (KBr discs) on a Shimadzu FT-IR 8201 PC spectrophotometer, Faculty of Science, Cairo University, Cairo, Egypt. NMR spectra were recorded on Varian Mercury-400 NMR Spectrometer and Bruker NMR spectrometer (Bruker BioSpin GmbH, Rheinstetten, Germany). $^1$H NMR spectra were run at 400 MHz, and $^{13}$C NMR spectra were run at 100 MHz in deuterated dimethyl sulfoxide (DMSO-$d_6$). Chemical shifts are expressed in δ values (ppm) relative to TMS. All coupling constant (J) values are given in hertz (Hz). The abbreviations used are as follows: s, singlet; d, doublet; t, triplet; m, multiplet; and dd; doublet-doublet. Electrospray ionization mass (ESI-MS) was obtained using LC-MS (Thermo Scientific Inc., Waltham, Massachusetts). The analytical purity of target compounds was determined by reversed phase HPLC in conjunction with product analysis by ESI-MS. UV absorption was detected from 200 to 800 nm using a diode array detector. The purity of the compounds was determined at 254 nm, and we observed pure peak for each compound attributed to its mass.

Example 3

2-(4-aminophenyl)-N-benzylacetamide (Int-1)

10 mmol (1.81 g) of 2-(4-nitrophenyl)acetic acid and 50 mL of dichloromethane (DCM) were combined in a dry round bottom flask. The flask was then evacuated with nitrogen and stirred in an ice bath. Subsequently, 11.6 mmol (1.48 g, 1 mL) of oxalyl chloride, together with 5 mL of dichloromethane (DCM), were introduced into a separate funnel and rapidly added to the initial mixture. A single drop of dimethylformamide (DMF) was added. After 15 minutes, the ice bath was removed and the mixture was agitated at room temperature (r.t.) for 5 hours until all the acid was completely dissolved. The solvent was eliminated through the utilization of a rotary evaporator, and the remaining substance, 2-(4-nitrophenyl)acetyl chloride, was dissolved in 40 mL of dichloromethane (DCM) and agitated for a duration of 10 minutes within a container placed in an ice bath.

The acid chloride was enriched with benzyl amine (10 mmol, 1.1 g, 1.1 mL) and Diisopropylethylamine (DIPEA) (10 mmol, 1.55 g, 2.1 mL) in 10 mL DCM drop by drop. Following the melting of the ice, the stirring process persisted throughout the night at the ambient temperature. The solid particles were separated through the process of filtration and subsequently washed using a little quantity of DCM, resulting in the formation of a crystalline solid weighing 1.14 g. The reaction's completion was verified by TLC for both the solid and filtrate, using a 1:1 ethyl acetate hexane mixture in comparison to the starting materials. The filtrate was neutralized with dil. HCl, and the organic layer was collected. The organic layer was dried using sodium sulphate, and the solvent was rotavaped. The solid was collected and rinsed with ether to afford N-benzyl-2-(4-nitrophenyl)acetamide as a yellowish white solid, yield: 85%. $^1$H NMR (400 MHz, DMSO-$d_6$) δ 8.66 (s, 1H), 8.19 (d, J=8.6 Hz, 2H), 7.56 (d, J=8.4 Hz, 2H), 7.39-7.14 (m, 6H), 4.29 (d, J=5.8 Hz, 2H), 3.67 (s, 2H).

In a 150 ml round bottom flask rapped with Aluminum foil, N-benzyl-2-(4-nitrophenyl)acetamide (6.58 mmol, 178 g), SnCl$_2$ dihydrate (26.34 mmol, 5.95 g), ethyl acetate (40 m L), and water (0.5 mL) were refluxed for 4 hrs. The mixture was cooled and diluted by ethyl acetate (40 mL) and then treated with a cold 40% NaOH solution (80 mL). Then fresh water was added to break an emulsion formed. The organic layer was separated then the aqueous layer was washed with 10 mL of ethyl acetate then the combined organic layers were washed with 15 mL of brine and dried with Magnesium sulphate. The ethyl acetate was distilled off using the rotary evaporator and the solid product was collected to afford Int-1 as a white solid, yield: 1.55 g (98.7%) $^1$H NMR (400 MHz, DMSO-$d_6$) δ 8.34 (s, 1H), 7.37-7.16 (m, 5H), 6.93 (d, J=8.4 Hz, 2H), 6.50 (d, J=8.3 Hz, 2H), 4.89 (s, 2H), 4.25 (d, J=5.9 Hz, 2H), 3.27 (s, 2H).

Example 4

Synthesis of 2-(4-azidophenyl)-N-benzylacetamide (Int-2)

To a solution of amine Int-1 (4.2 mmol, 1 g) in H$_2$O (5 mL) was added sequentially concentrated HCl (21 mmol, 17 mL), NaNO$_2$ (5.04 mmol, 348 g) at 0° C. The reaction mixture was stirred at 0° C. for 0.5 h. A solution of NaN$_3$ (6.72 mmol, 436.8 g) in H$_2$O (10 mL) was added dropwise to the mixture at 0° C. This reaction mixture was stirred at 0° C. for 0.5 h and stirred at room temperature for 4 h. Then DCM (50 mL) was added, the organic phase was separated and aqueous layer was extracted with DCM (30 mL×2). The combined organic layers were concentrated to afford the Int-2 as orange solid (Yield 97%)

Example 5

General Procedure for the Synthesis of the Alkyne Intermediates (Int-3)

To a solution of phenol derivative (0.01 mol) in Acetone (20 mL), potassium carbonate (2.07 g, 0.015 mol) was added and stirred for 30 minutes at r.t. Propargyl bromide (0.86 ml, 0.01 mol) was then added dropwise, over 5 minutes, and the resulting mixture was stirred at 80° C. for 12 h, TLC monitored (5% ethyl acetate/hexane). The resulting mixture was washed with water (50 mL), extracted with ethyl acetate (50 mL), and the final mixture was dried under vacuum, to finally afford the Int-3

Example 6

General Procedure for Synthesis of Comp-1 to Comp-8

A mixture of 2-(4-azidophenyl)-N-benzylacetamide Int-2 (1.64 g, 0.01 mol), propargyl alcohol or Int-3 alkyne derivatives (0.012 mol) and CuI (0.19 g, 0.001 mol) in DMF (30 mL) was heated under reflux for 12 h, TLC monitored (20% ethyl acetate/hexane). The resulting mixture was filtered using celite to remove CuI. and extracted with EtOAc (3×). The organics were washed with $H_2O$ and brine, dried ($MgSO_4$) and evaporated to give a crude solid. This was purified by silica gel chromatography (hexane/EtOAc) to furnish the disclosed Comp-1 to Comp-8.

N-benzyl-2-(4-(4-(hydroxymethyl)-1H-1,2,3-triazol-1-yl)phenyl)acetamide (Comp-1)

Grey Solid, Yield: 72%; $^1$H NMR (400 MHz, DMSO-$d_6$) δ 8.62 (2H, triazole proton and NH D2O exchangeable proton), 7.83 (d, J=8.5 Hz, 2H), 7.48 (d, J=8.5 Hz, 2H), 7.36-7.15 (m, 5H), 5.33 (t, J=5.6 Hz, 1H, OH D2O exchangeable proton), 4.61 (d, J=5.3 Hz, 2H, —CH2-O,), 4.29 (d, J=5.9 Hz, 2H, —CH2-NH), 3.58 (s, 2H, —CH2-CO). MS (ESI) m/z: 323 [M+H] at retention time 2.09 min.

N-benzyl-2-(4-(4-(phenoxymethyl)-1H-1,2,3-triazol-1-yl)phenyl)acetamide (Comp-2)

brown Solid, Yield: 78%; $^1$H NMR (400 MHz, DMSO-$d_6$) δ 8.91 (s, 1H, triazole proton), 8.62 (s, 1H, D2O exchangeable proton), 7.85 (d, J=8.3 Hz, 2H), 7.50 (d, J=8.2 Hz, 2H), 7.38-7.29 (m, 4H), 7.26 (t, J=7.8 Hz, 3H), 7.08 (d, J=8.0 Hz, 2H), 6.98 (t, J=7.3 Hz, 1H), 5.23 (s, 2H, —CH2-O), 4.29 (d, J=5.9 Hz, 2H, —CH2-NH), 3.59 (s, 2H, —CH2-CO). $^{13}$C NMR (126 MHz, DMSO) δ 170.16, 160.59, 158.46, 144.34, 139.82, 139.21, 137.65, 135.55, 130.91, 130.04, 128.78, 128.76, 127.83, 127.72, 127.38, 127.29, 123.29, 121.43, 120.52, 115.16, 61.37, 42.85, 42.73. MS (ESI) m/z: 399 [M+H] at retention time 3.24 min.

N-benzyl-2-(4-(4-((m-tolyloxy)methyl)-1H-1,2,3-triazol-1-yl)phenyl)acetamide (Comp-3)

brown Solid, Yield: 69%; $^1$H NMR (400 MHz, DMSO-$d_6$) δ 8.90 (s, 1H, triazole proton), 8.62 (s, 1H, D2O exchangeable proton), 7.85 (d, J=7.9 Hz, 2H), 7.50 (d, J=8.1 Hz, 2H), 7.31 (d, J=7.2 Hz, 2H), 7.25 (d, J=7.3 Hz, 3H), 7.15 (dd, J=27.2, 8.1 Hz, 1H), 7.01-6.72 (m, 3H), 5.21 (s, 2H, —CH2-O), 4.29 (s, 2H, —CH2-NH), 3.59 (s, 2H, —CH2-CO), 2.30 (s, 3H). $^{13}$C NMR (126 MHz, DMSO) δ 170.16, 158.50, 144.42, 139.82, 139.54, 137.64, 135.56, 130.90, 130.35, 129.75, 128.78, 127.72, 127.29, 123.22, 122.18, 120.51, 115.83, 115.05, 112.16, 61.48, 61.35, 42.74, 42.15, 21.61. MS (ESI) m/z: 413 [M+H] at retention time 3.42 min.

N-benzyl-2-(4-(4-((p-tolyloxy)methyl)-1H-1,2,3-triazol-1-yl)phenyl)acetamide (Comp-4)

brown Solid, Yield: 75%; $^1$H NMR (400 MHz, DMSO-$d_6$) δ 8.89 (s, 1H, triazole proton), 8.61 (s, 1H, D2O exchangeable proton), 7.84 (d, J=8.1 Hz, 2H), 7.50 (d, J=8.1 Hz, 2H), 7.38-7.17 (m, 5H, phenyl), 7.12 (d, J=8.3 Hz, 2H), 6.97 (d, J=7.7 Hz, 2H), 5.19 (s, 2H, —CH2-O), 4.29 (d, J=4.4 Hz, 2H, —CH2-NH), 3.59 (s, 2H, —CH2-CO), 2.24 (s, 3H, —CH3).

N-benzyl-2-(4-(4-((benzyloxy)methyl)-1H-1,2,3-triazol-1-yl)phenyl)acetamide (Comp-5)

Grey Solid, Yield: 80%; $^1$H NMR (400 MHz, DMSO-$d_6$) δ 8.83 (s, 1H, triazole proton), 8.63 (s, 1H, D2O exchangeable proton), 7.85 (d, J=7.9 Hz, 2H), 7.49 (d, J=8.1 Hz, 2H), 7.38 (s, 2H), 7.35-7.27 (m, 4H), 7.28-7.18 (m, 4H), 4.67 (s, 2H, —CH2-O), 4.60 (s, 2H, —CH2-NH), 4.29 (s, 2H, between triazole and O), 3.58 (s, 2H, —CH2-CO). $^{13}$C NMR (126 MHz, DMSO) δ 170.18, 139.83, 138.54, 137.51, 135.65, 130.87, 128.78, 128.20, 128.01, 127.73, 127.27, 122.74, 120.44, 71.84, 63.28, 42.73, 42.15. MS (ESI) m/z: 413 [M+H] at retention time 3.21 min.

N-benzyl-2-(4-(4-((naphthalen-2-yloxy)methyl)-1H-1,2,3-triazol-1-yl)phenyl)acetamide (Comp-6)

Brown Solid, Yield: 81%; $^1$H NMR (400 MHz, DMSO-$d_6$) δ 9.03 (s, 1H, triazole proton), 8.62 (t, J=5.9 Hz, 1H, D2O exchangeable proton), 8.21 (d, J=8.1 Hz, 1H), 7.89 (d, J=8.4 Hz, 3H), 7.57-7.42 (m, 6H), 7.35-7.28 (m, 2H), 7.28-7.17 (m, 4H), 5.45 (s, 2H, —CH2-O), 4.30 (d, J=5.8 Hz, 2H, —CH2-NH), 3.60 (s, 2H, —CH2-CO). $^{13}$C NMR (126 MHz, DMSO) δ 170.19, 153.96, 144.47, 139.84, 137.67, 135.61, 134.54, 130.90, 128.77, 127.72, 127.70, 127.29, 126.99, 126.63, 125.85, 122.16, 120.92, 120.55, 106.28, 62.17, 42.74, 42.17. MS (ESI) m/z: 449 [M+H] at retention time 3.66 min.

N-benzyl-2-(4-(4-(((2-oxo-2H-chromen-4-yl)oxy)methyl)-1H-1,2,3-triazol-1-yl)phenyl)acetamide (Comp-7)

Grey Solid, Yield: 72%; $^1$H NMR (400 MHz, DMSO-$d_6$) δ 8.97 (s, 1H), 8.62 (s, 1H, D2O exchangeable proton), 8.01 (d, J=9.6 Hz, 1H), 7.85 (d, J=8.2 Hz, 2H), 7.67 (d, J=8.5 Hz, 1H), 7.50 (d, J=8.2 Hz, 2H), 7.31 (d, J=7.1 Hz, 2H), 7.29-7.18 (m, 3H), 7.11-7.04 (m, 2H), 6.32 (d, J=9.5 Hz, 1H, chromenone proton), 5.37 (s, 2H), 5.12 (s, 1H), 4.29 (d, J=6.0 Hz, 2H), 3.59 (s, 2H).

N-benzyl-2-(4-(4-((benzyloxy)methyl)-1H-1,2,3-triazol-1-yl)phenyl)acetamide (Comp-8)

Brown Solid, Yield: 775%; $^1$H NMR (400 MHz, DMSO-$d_6$) δ 8.92 (s, 1H, triazole proton), 8.55 (s, 1H, D2O exchangeable proton), 7.75 (d, J=7.9 Hz, 2H), 7.25 (d, J=8.1 Hz, 2H), 7.31 (d, J=7.2 Hz, 2H), 7.25 (d, J=7.3 Hz, 3H), 7.15 (dd, J=27.2, 8.1 Hz, 1H), 7.01-6.72 (m, 3H), 5.21 (s, 2H, —CH2-O), 4.29 (s, 2H, —CH2-NH), 3.59 (s, 2H, —CH2-CO), 2.30 (s, 3H). MS (ESI) m/z: 413 [M+H] at retention time 3.21 min.

Example 7

Biological Screening: General

All reagents used in the biological screenings were purchased from Millipore-Sigma (UK) of molecular biology grade unless stated otherwise.

Example 8

Cell Culture

The MCF-7 breast cancer cell lines were purchased from VACSERA Tissue Culture Unit (Giza, Egypt). MCF-7 cells were cultured in RPMI medium supplemented with 2 mM glutamine and 10% fetal bovine serum. Both cell cultures included 100 mg/ml streptomycin and 100 units/ml penicillin and were kept in a humidified atmosphere with 5% $CO_2$ at 37° C.

Example 9

Cytotoxicity Test

As an indicator of cytotoxic activity, cell viability was determined using the MTT [(3-(4,5-dimethylthiazol-2-yl)-2, 5-diphenyltetrazolium bromide] assay according to the instructions provided by the manufacturer. Briefly, MCF-7 cells were plated at $5 \times 10^3$ cells/well in 96-well plates. Cells were treated with test compounds or Staurosporine at 0.01, 0.1, 1.0, 10 and 100 M concentrations for 24 h. The plates were read at 570 nm. Denoted data are the means of the three experiments. $IC_{50}$ values were calculated by nonlinear regression analysis using Graph Pad Prism version 5 for windows (Graph Pad Inc., CA, USA). All experiments were performed in triplicate. Data were given as mean±SD.

Example 10

Assessment of MCL-1 and BCL-2 Inhibition by TR-FRET Assay

The effectiveness of inhibiting the MCL-1 and BCL-2 proteins was evaluated using specific assay kits (BPS Bioscience, Sandiego, CA) and corresponding ligands for each protein. The test compounds were incubated with the proteins for 120 or 180 min, and the experiment was repeated three times using Sabutoclax as a positive control. The concentrations of the test compounds Comp-1 and Comp-6 and positive control ranged from 0.01, 0.1, 1.0, 10 µM. Measurements were taken of Tb-donor emission at 620 nm followed by dye-acceptor emission at 665 nm, and data analysis was performed using the TR-FRET ratio (665 nm emission/620 nm emission). The FRET value from the positive control was considered as full activity (100%) and the FRET value from the negative control was considered as zero percent activity. Then, % inhibitory activity of test compounds was calculated by the equation:

$$\% \text{ Activity} = FRET_S - FRET_{neg}/FRET_P - FRET_{neg} \times 100\%$$

Where $FRET_S$, $FRET_{neg}$, and $FRET_P$ are sample FRET, negative control FRET, and positive control FRET, respectively. The $IC_{50}$ values of the test compounds were calculated by nonlinear regression analysis on GraphPad Prism 5 (GraphPad Inc., USA).

Example 11

Assessment of Effect of Exemplary Compounds on Cellular Content of BCL-2, MCL-1 and MAPK Protein Using Western Blot Analysis MCF-7 cells were exposed to compounds Comp-1 and Comp-6 for a period of 24 h, after which western blot analysis was conducted using a previously established protocol[21]. To assess the release of cytochrome c, cytosolic and mitochondrial fractions were prepared in accordance with the methods outlined by Kawiak et al[21]. Specific primary antibodies were utilized viz; anti-β-actin (1:1,000) (Cell Signaling, Danvers, MA, USA), anti-Bcl-2, anti-Bax, and anti-Mcl-1 (1:250) (Santa Cruz, Heidelberg, Germany), anti-ERK1/2, anti-MEK1/2, anti-p-ERK1/2, and anti-p-MEK1/2 (1:1,000) (Cell Signaling), and anti-cytochrome c (1:5,000) (Abcam, UK), and membranes were subjected to an overnight incubation with these antibodies at 4° C. This was followed by a 1 h incubation with HRP-conjugated secondary antibodies (1:2000) (Cell Signaling). The levels of protein were then determined using chemiluminescence (ChemiDoc; Bio-Rad, Waltham, MA, USA) with an HRP substrate (Thermo Scientific, MA, USA).

Example 12

Biological Screening Results

The disclosed compounds (Comp-1 to Comp-8) exhibited a range of cytotoxic activities against MCF7 breast cancer cells. Notably, Comp-1 (alcohol) demonstrated the highest potency, with an inhibition concentration 50 ($IC_{50}$) value of 1.095 µM, approximately 5-fold higher than the reference drug Staurosporine ($IC_{50}$=5.69 µM). Comp-6 (naphthalyl ether) emerged as the second most potent compound, with an $IC_{50}$ value of 1.88 µM. Additionally, Comp-5 (benzyl ether) displayed superior activity compared to Staurosporine, with an $IC_{50}$ value of 3.2 µM. The remaining compounds showed significant cytotoxic activities, although their potencies were lower than that of Staurosporine.

The cytotoxic activities findings suggest that Comp-1, Comp-6, and Comp-5 are promising candidates for further investigation as potential therapeutic agents against breast cancer.

The cytotoxic mechanisms of the exemplary compounds Comp-1 and Comp-6 were investigated. Given that apoptosis is a common mechanism of action for many cancer therapies, we analyzed the levels of apoptotic markers BAX, BCL-2 and MCL-1 after treating MCF7 cells with Comp-1 and Comp-6 for 24 hours. Western blot analysis was performed on cell lysates and compared to untreated cell lysates. The results showed that BAX, a crucial proapoptotic protein, was significantly upregulated by Comp-1 and Comp-6, with a more than five-fold and nine-fold increase, respectively, compared to untreated cells (Control). Conversely, the antiapoptotic proteins BCL-2 and MCL-1 were downregulated, with Comp-1 reducing BCL-2 and MCL-1 expression by 65.3% and 65.4%, respectively, and Comp-6 reducing their expression by 55.9% and 43.7%, respectively. These findings suggest that Comp-1 and Comp-6 induce apoptosis in MCF7 cells by modulating the expression of key apoptotic regulators.

To investigate the impact of exemplary compounds on the cancer-promoting MAPK pathway in MCF7 breast cancer cells, we stimulated the cells with epidermal growth factor (EGF) for 30 minutes to induce p-ERK1/2 and p-MEK1/2 protein expression. Western blot analysis of cell lysates revealed that Comp-1 and Comp-6 significantly inhibited the MAPK pathway. Specifically, Comp-1 reduced p-MEK1/2 signal by 65.3% and p-ERK1/2 signal by 46.1%, while Comp-6 reduced p-MEK signal by 55.9% and p-ERK1/2 signal by 50.7%. These findings suggest that Comp-1 and Comp-6 suppress the activation of the MAPK pathway, a key signaling cascade involved in cancer cell proliferation and survival.

The exemplary compounds Comp-1 and Comp-6 were examined for their direct inhibition activities against BCL-2 and MCL-1 using a free cell TR-FRET assay method. Sabutoclax, a known inhibitor of these two targets was used a positive reference Comp-1 inhibited the BCL-2 and MCL-1 proteins at $IC_{50}$ values 0.507 µM, and 0.365 µM, respectively. This is slightly lower inhibitory potency than Sabutoclax which exhibited $IC_{50}$ 0.278 µM (BCL-2) and 0.251 µM (MCL-1). Comp 6 inhibited the two proteins at $IC_{50}$ value of 1.922 µM and 0.756 µM against BCL-2 and MCL-1, respectively[22].

In conclusion, this disclosure explains the therapeutic benefits of Formulae I and II compounds. The exemplary compound Comp-1 demonstrated higher potencies than a reference drug in breast cancer growth inhibition, high induction of apoptotic mechanisms and reduction in cancer promoting signals such as MAPK pathway.

ACKNOWLEDGMENT OF SPONSORED RESEARCH

This invention was funded by the University of Jeddah, Jeddah, Saudi Arabia, under grant No. (UJ-23-RSP-7). The inventors, therefore, thank the University of Jeddah for its technical and financial support.

REFERENCES

ADDIN EN.REFLIST 1. Roulot, A.; Héquet, D.; Guinebretière, J. M.; Vincent-Salomon, A.; Lerebours, F.; Dubot, C.; Rouzier, R., Tumoral heterogeneity of breast cancer. *Annales de biologie clinique* 2016, 74 (6), 653-660.
2. Sung, H.; Ferlay, J.; Siegel, R. L.; Laversanne, M.; Soerjomataram, I.; Jemal, A.; Bray, F., Global Cancer Statistics 2020: GLOBOCAN Estimates of Incidence and Mortality Worldwide for 36 Cancers in 185 Countries. *CA: a cancer journal for clinicians* 2021, 71 (3), 209-249.
3. DeSantis, C. E.; Ma, J.; Gaudet, M. M.; Newman, L. A.; Miller, K. D.; Goding Sauer, A.; Jemal, A.; Siegel, R. L., Breast cancer statistics, 2019. *CA: a cancer journal for clinicians* 2019, 69 (6), 438-451.
4. Siegel, R. L.; Giaquinto, A. N.; Jemal, A., Cancer statistics, 2024. *CA: a cancer journal for clinicians* 2024, 74 (1), 12-49.
5. Orrantia-Borunda, E.; Anchondo-Nuñez, P.; Acuña-Aguilar, L. E.; Gómez-Valles, F. O.; Ramírez-Valdespino, C. A., Subtypes of Breast Cancer. In *Breast Cancer*, Mayrovitz, H. N., Ed. Exon Publications Copyright: The Authors.; The authors confirm that the materials included in this chapter do not violate copyright laws. Where relevant, appropriate permissions have been obtained from the original copyright holder(s), and all original sources have been appropriately acknowledged or referenced.: Brisbane (AU), 2022.
6. Obeagu, E. I.; Obeagu, G. U., Breast cancer: A review of risk factors and diagnosis. *Medicine* 2024, 103 (3), e36905.
7. Feng, Y; Spezia, M.; Huang, S.; Yuan, C.; Zeng, Z.; Zhang, L.; Ji, X.; Liu, W.; Huang, B.; Luo, W.; Liu, B.; Lei, Y; Du, S.; Vuppalapati, A.; Luu, H. H.; Haydon, R. C.; He, T. C.; Ren, G., Breast cancer development and progression: Risk factors, cancer stem cells, signaling pathways, genomics, and molecular pathogenesis. *Genes & diseases* 2018, 5 (2), 77-106.
8. Board, P. D. Q. A. T. E., Breast Cancer Treatment (PDQ®): Health Professional Version. In *PDQ Cancer Information Summaries*, National Cancer Institute (US): Bethesda (MD), 2002.
9. Menon, G.; Alkabban, F. M.; Ferguson, T., Breast Cancer. In *StatPearls*, StatPearls Publishing Copyright © 2024, StatPearls Publishing LLC.: Treasure Island (FL)
10. Neve, R. M.; Chin, K.; Fridlyand, J.; Yeh, J.; Baehner, F. L.; Fevr, T.; Clark, L.; Bayani, N.; Coppe, J. P.; Tong, F.; Speed, T.; Spellman, P. T.; DeVries, S.; Lapuk, A.; Wang, N. J.; Kuo, W. L.; Stilwell, J. L.; Pinkel, D.; Albertson, D. G.; Waldman, F. M.; McCormick, F.; Dickson, R. B.; Johnson, M. D.; Lippman, M.; Ethier, S.; Gazdar, A.; Gray, J. W., A collection of breast cancer cell lines for the study of functionally distinct cancer subtypes. *Cancer cell* 2006, 10 (6), 515-27.
11. Perou, C. M.; Sørlie, T.; Eisen, M. B.; van de Rijn, M.; Jeffrey, S. S.; Rees, C. A.; Pollack, J. R.; Ross, D. T.; Johnsen, H.; Akslen, L. A.; Fluge, O.; Pergamenschikov, A.; Williams, C.; Zhu, S. X.; Lønning, P. E.; Børresen-Dale, A. L.; Brown, P. O.; Botstein, D., Molecular portraits of human breast tumours. *Nature* 2000, 406 (6797), 747-52.
12. Wang, S.; Chen, X.; Zhang, X.; Wen, K.; Chen, X.; Gu, J.; Li, J.; Wang, Z., Pro-apoptotic gene BAX is a pan-cancer predictive biomarker for prognosis and immunotherapy efficacy. *Aging* 2024, 16 (14), 11289-11317.
13. Reed, J. C., Bcl-2 family proteins: regulators of apoptosis and chemoresistance in hematologic malignancies. *Seminars in hematology* 1997, 34 (4 Suppl 5), 9-19.
14. Zhang, L.; Lu, Z.; Zhao, X., Targeting Bcl-2 for cancer therapy. *Biochimica et biophysica acta. Reviews on cancer* 2021, 1876 (1), 188569.
15. Alcon, C.; Gómez Tejeda Zañudo, J.; Albert, R.; Wagle, N.; Scaltriti, M.; Letai, A.; Samitier, J.; Montero, J., ER+ Breast Cancer Strongly Depends on MCL-1 and BCL-xL Anti-Apoptotic Proteins. *Cells* 2021, 10 (7).
16. Campbell, K. J.; Dhayade, S.; Ferrari, N.; Sims, A. H.; Johnson, E.; Mason, S. M.; Dickson, A.; Ryan, K. M.; Kalna, G.; Edwards, J.; Tait, S. W. G.; Blyth, K., MCL-1 is a prognostic indicator and drug target in breast cancer. *Cell death & disease* 2018, 9 (2), 19.
17. Williams, M. M.; Cook, R. S., Bcl-2 family proteins in breast development and cancer: could Mcl-1 targeting overcome therapeutic resistance? *Oncotarget* 2015, 6 (6), 3519-30.
18. Johnson, G. L.; Lapadat, R., Mitogen-activated protein kinase pathways mediated by ERK, INK, and p38 protein kinases. *Science (New York, N.Y.)* 2002, 298 (5600), 1911-2.
19. Santen, R. J.; Song, R. X.; McPherson, R.; Kumar, R.; Adam, L.; Jeng, M. H.; Yue, W., The role of mitogen-activated protein (MAP) kinase in breast cancer. *The Journal of steroid biochemistry and molecular biology* 2002, 80 (2), 239-56.
20. Song, Y; Bi, Z.; Liu, Y; Qin, F.; Wei, Y; Wei, X., Targeting RAS-RAF-MEK-ERK signaling pathway in human cancer: Current status in clinical trials. *Genes & diseases* 2023, 10 (1), 76-88.
21. Kawiak, A.; Kostecka, A., Regulation of Bcl-2 Family Proteins in Estrogen Receptor-Positive Breast Cancer and Their Implications in Endocrine Therapy. *Cancers* 2022, 14 (2).
22. Hu, Y; Yagüe, E.; Zhao, J.; Wang, L.; Bai, J.; Yang, Q.; Pan, T.; Zhao, H.; Liu, J.; Zhang, J., Sabutoclax, pan-active BCL-2 protein family antagonist, overcomes drug resistance and eliminates cancer stem cells in breast cancer. *Cancer letters* 2018, 423, 47-59.

The invention claimed is:

1. A compound of formula (I)

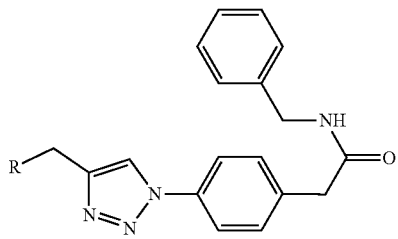

or a salt thereof or a composition thereof,
wherein R is a group selected from the group consisting of alkyl, alkoxy, alkylamino, alkylthio, phenyl, phenoxy, phenylamino, phenylthiol, hydroxy, amino, aralkyl, heterocyclic, amidic, ureidic, carboxylic sulfonamido, or ester, and wherein the group is optionally substituted with an alkyl, aryl, alkoxy, nitrile, nitro, or halo group.

2. A compound of formula (II)

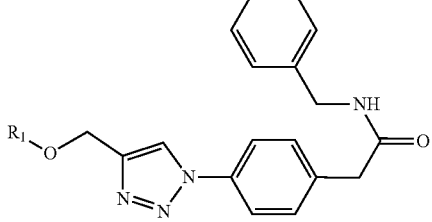

wherein R1 is selected from the group consisting of H, alkyl, phenyl, substituted phenyl, aralkyl, heterocyclic, and heterocyclic methyl.

3. The compound of claim 2, wherein $R_1$ is a hydrogen, phenyl, substituted phenyl, benzyl, naphthyl, chromenyl, or substituted chromenyl.

4. The compound of claim 1, which is

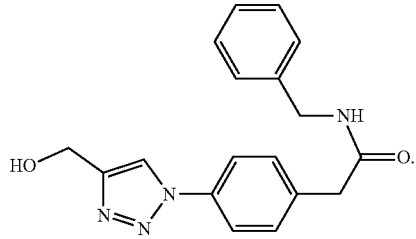 [SMILES: O=C(Cc1ccc(-n2cc(CO)nn2)cc1)NCc1ccccc1]

5. A pharmaceutical composition, comprising:
one or more compounds of claim 1; and
a pharmaceutically acceptable carrier and/or excipient.

6. A compound having a structure selected from the group consisting of:

Comp 1

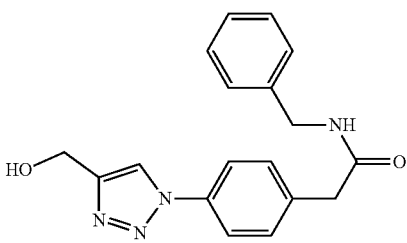

Comp 2

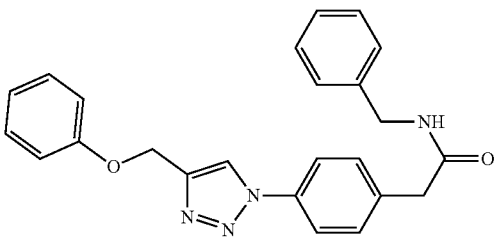

Comp 3

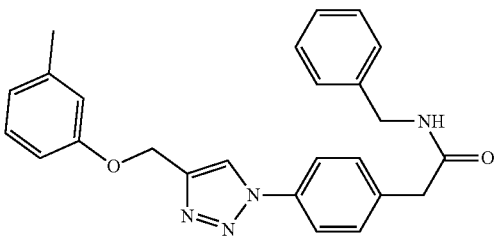

Comp 4

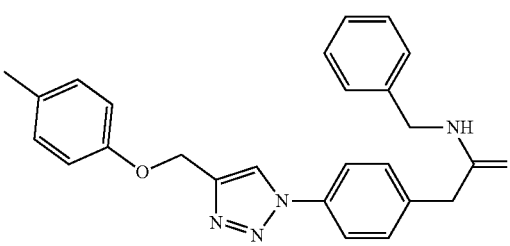

Comp 5

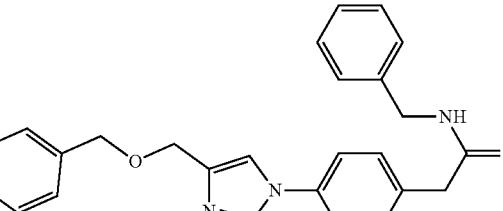

Comp 6

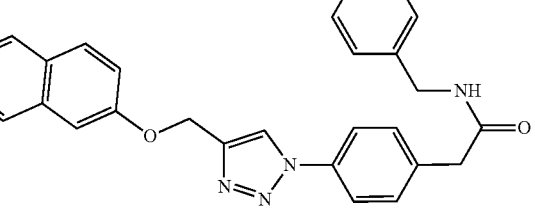

Comp 7
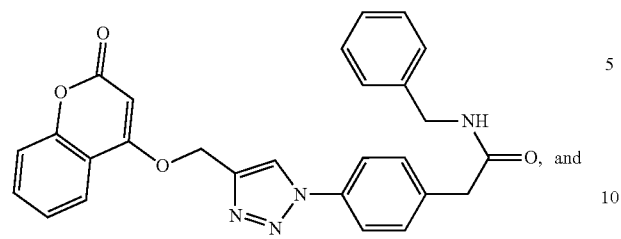
Comp 8
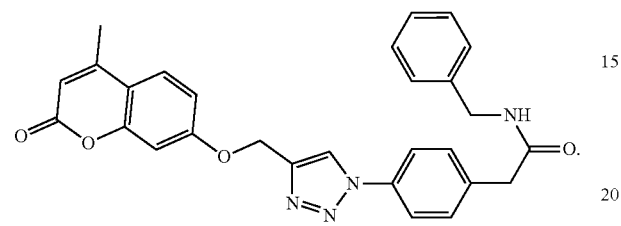
* * * * *